(12) United States Patent
Scurtescu et al.

(10) Patent No.: US 11,478,435 B2
(45) Date of Patent: *Oct. 25, 2022

(54) ARTIFICIAL SALIVA, RELATED METHODS, AND USES

(71) Applicant: SMILESONICA INC., Edmonton (CA)

(72) Inventors: Cristian Scurtescu, Edmonton (CA); Gleam Gill, Edmonton (CA)

(73) Assignee: Smilesonica Inc., Edmonton (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/487,188

(22) PCT Filed: Feb. 21, 2018

(86) PCT No.: PCT/CA2018/050195
§ 371 (c)(1),
(2) Date: Aug. 20, 2019

(87) PCT Pub. No.: WO2018/152627
PCT Pub. Date: Aug. 30, 2018

(65) Prior Publication Data
US 2020/0281868 A1 Sep. 10, 2020

Related U.S. Application Data

(60) Provisional application No. 62/461,987, filed on Feb. 22, 2017.

(51) Int. Cl.
*A61K 31/047* (2006.01)
*A61K 9/06* (2006.01)
(Continued)

(52) U.S. Cl.
CPC ............ *A61K 31/047* (2013.01); *A61K 9/006* (2013.01); *A61K 9/06* (2013.01); *A61K 9/14* (2013.01);
(Continued)

(58) Field of Classification Search
CPC ............. A61K 9/06; A61K 9/006; A61K 9/14
(Continued)

(56) References Cited

U.S. PATENT DOCUMENTS

| 4,002,221 A | 1/1977 | Buchalter |
| 5,482,965 A | 1/1996 | Rajadhyaksha |

(Continued)

FOREIGN PATENT DOCUMENTS

| CA | 2484869 A1 | 11/2003 |
| CA | 2872142 A1 | 11/2013 |

(Continued)

OTHER PUBLICATIONS

Hu et al. "Synergistic stabilization of emulsion and emulsion gels with water-soluble polymers and cellulose Nanocrystals," Sustainable Chemistry & Engineering, 2015, vol. 3, pp. 1023-1031. (Year: 2015).*

(Continued)

*Primary Examiner* — Shengjun Wang
(74) *Attorney, Agent, or Firm* — Russell Manning; FisherBroyles, LLP

(57) ABSTRACT

The present disclosure relates to an artificial saliva gel and uses thereof to treat or ameliorate dry mouth (xerostomia). The gel can be of a high viscosity that is maintained at body temperature or when exposed to bodily fluids (for instance, saliva). In some embodiments, the gel can act as a lubricant. Although water-based, the gel can be hydrophobic and not readily dissolvable in bodily fluids. In some embodiments, the gel can be sterile, safe for long-term repeated ingestion, and include a preservative. In some embodiments, the gel can comprise a dental agent for inhibiting growth of dental microorganisms. In order to achieve sterility while maintaining a desired viscosity range, the gel can include a viscosity stabilising agent such as a viscosity protection (Continued)

agent for protection from radiation induced breakdown. The gel can also include a coloring and/or a flavoring agent.

19 Claims, 1 Drawing Sheet

(51) Int. Cl.
    *A61K 9/00*         (2006.01)
    *A61K 9/14*         (2006.01)
    *A61K 47/10*       (2017.01)
    *A61K 47/32*       (2006.01)
    *A61K 47/38*       (2006.01)

(52) U.S. Cl.
    CPC .............. *A61K 47/10* (2013.01); *A61K 47/32* (2013.01); *A61K 47/38* (2013.01)

(58) Field of Classification Search
    USPC ..................................... 424/78.18, 400, 499
    See application file for complete search history.

(56) References Cited

U.S. PATENT DOCUMENTS

| | | | |
|---|---|---|---|
| 8,273,024 | B2 | 9/2012 | Chew et al. |
| 8,828,434 | B2 | 9/2014 | Shunxing |
| 10,265,547 | B2 | 4/2019 | Scurtescu et al. |
| 2005/0171419 | A1 | 8/2005 | De Ziegler |
| 2006/0127316 | A1 | 6/2006 | Smith |
| 2008/0281197 | A1 | 11/2008 | Wiley et al. |
| 2009/0099149 | A1 | 4/2009 | Liu et al. |
| 2009/0297441 | A1 | 12/2009 | Canham et al. |
| 2011/0052740 | A1 | 3/2011 | Mori et al. |
| 2012/0150033 | A1 | 6/2012 | Rauch |
| 2012/0237612 | A1 | 9/2012 | Lampe |
| 2016/0002457 | A1* | 1/2016 | Hamad .................. C08L 33/26 522/72 |
| 2019/0015529 | A1 | 1/2019 | Scurtescu et al. |

FOREIGN PATENT DOCUMENTS

| | | |
|---|---|---|
| CA | 2970146 A1 | 6/2016 |
| CN | 0393299 A1 | 10/1990 |
| CN | 101695576 A | 4/2010 |
| CN | 101716354 A | 6/2010 |
| CN | 102107013 A | 6/2011 |
| CN | 104840958 A | 8/2015 |
| CN | 102580122 A1 | 7/2017 |
| EP | 0396394 A2 | 11/1990 |
| EP | 1437126 A1 | 7/2004 |
| JP | 2008508338 | 3/2008 |
| WO | 2003094710 A2 | 11/2003 |
| WO | WO2006013081 A1 | 2/2006 |
| WO | 2007038855 A1 | 4/2007 |
| WO | 2011134071 A1 | 11/2011 |
| WO | 2014094127 A1 | 6/2014 |
| WO | WO2014085730 A1 | 6/2014 |
| WO | 2016094054 A1 | 6/2016 |
| WO | 2017117650 A1 | 7/2017 |

OTHER PUBLICATIONS

Yang et al. ("Injectable polysaccharide hydrogels reinforced with cellulose nanocrystals: Morphology, Rheology, degradation, and cytotoxicity," BioMacromolecules, 2013, vol. 4447-4455) (Year: 2013).*
Dufesne, "Nanocellulose: A New Ageless Bionanomaterial", Materials Today, 2003.
Kontiokari et al. "Effect of xylitol on growth of nasopharyngeal bacteria in vitro" Antimicrob Agents Chemother. Aug. 1995; 39(8)1820-3.
Lin et al. "Nanocellulose in biomedicine: Current status and future prospect" Eur. Polymer J., 2014, vol. 59,302-325.
Liu Jun, et al., "Nanoparticles as Image Enhancing Agents for Ultrasonography" Phys. Med. Biol. 51 (2006) 2179-2189.
Lubrizol "Ultrasound Gel with Carbopol 980 NF Polymer" Lubrizol Advanced Materials, Inc. Jun. 1, 2011.
Lubrizol "Ultrasound Gel with Carbopol ETD 2020 NF Polymer" Lubrizol Advanced Materials, Inc. Jun. 1, 2011.
Mahalingham et al. "Design of a Semisolid Vaginal Gel by Relating Composition to Properties and Performance" Pharm Res. 27 (2010) pp. 2478-2491.
Norman et al. "Progesterone for prevention of preterm birth in twin pregnancy"; Lancet 373 (2009) pp. 2034-2040.
Parker Laboratories Data sheet "Sterile Ultrasonic 100 Ultrasound Transmission Gel".
Söderling "Xylitol, Mutans Streptococci and Dental Plaque", Adv. Dent. Res 2009, 21 74-78, Aug. 2009.
The Lubrizol Corporation "Oral Suspensions", Pharmaceutical Bulletin 22, Edition May 31, 2011.
Yamaguchi, Aki, "One Step Ahead From the Front Line—The effective use of oral moisturizers"; Medical Online, vol. 30, No. 12, 2010, p. 1260-1263.
Yang et al. "Mechanical and Viscoelastic Properties of Cellulose Nanocrystals". ACS Appl. Mater. Interfaces 2013, 5,8, 3199-3207.
Nov. 11, 2020 Supplementary European Search Report EP 18 75 8045.
Shafiei-Sabet, S. et al. "Rheology of Nanocrystalline Cellulose Aqueous Suspensions", Langmuir, 28, 17124-17133.

* cited by examiner

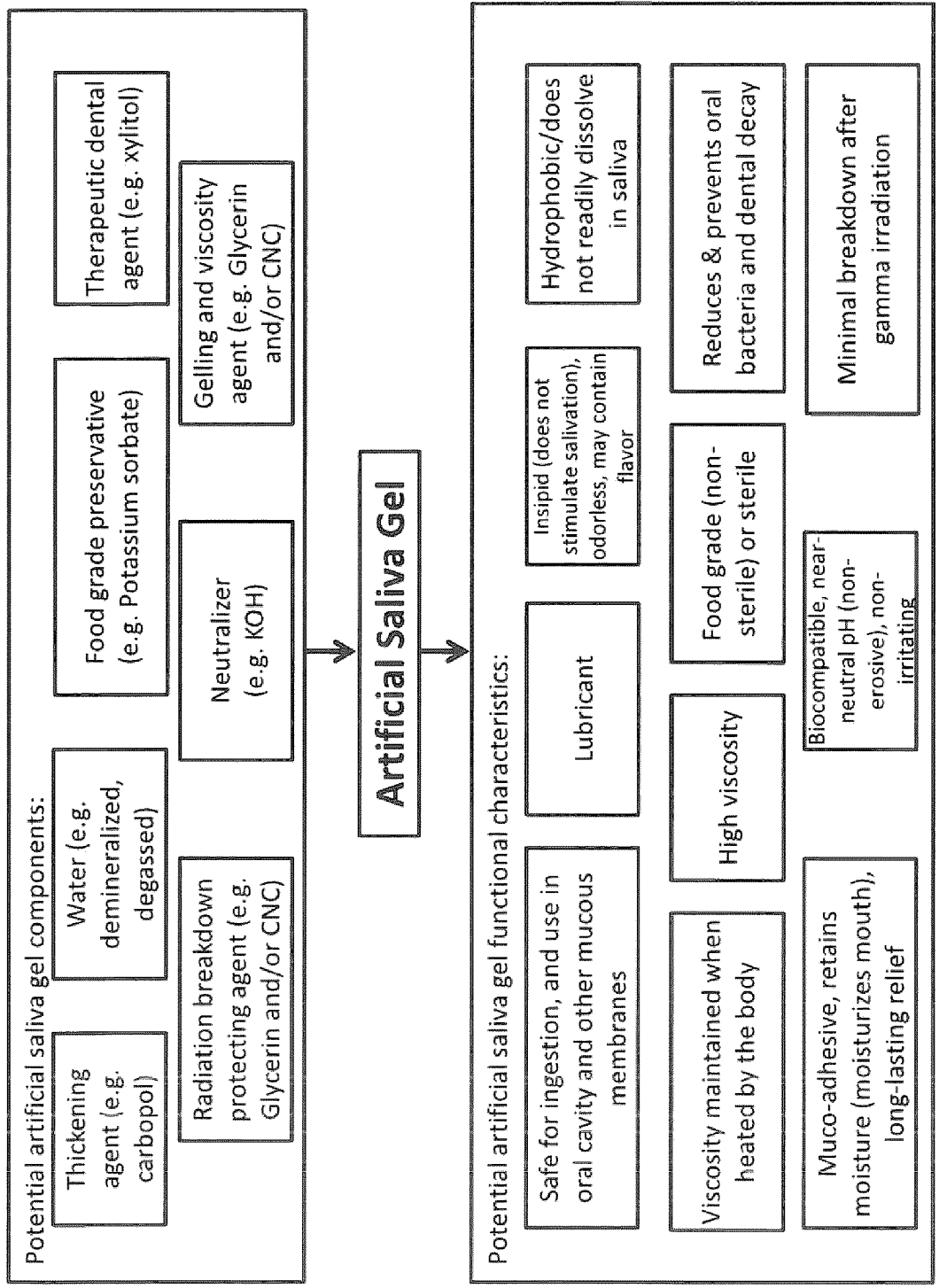

ARTIFICIAL SALIVA, RELATED METHODS, AND USES

CROSS REFERENCE TO RELATED APPLICATIONS

This application claims priority of U.S. Provisional Patent Application Ser. No. 62/461,987, entitled "Artificial Saliva and Related Methods and Uses", filed Feb. 22, 2017, and hereby incorporated by reference herein in its entirety.

TECHNICAL FIELD

The present application relates to artificial saliva, and more particularly, to artificial saliva gels that can be used safely and effectively.

BACKGROUND

By way of background, the occurrence of dry mouth (xerostomia) is significant. One in five people (20% of the population) suffer from dry mouth and the occurrence is expanding with an ageing population.

The main causes of dry mouth are side-effects of common medications, radiation exposure of salivary glands during treatment of head and neck cancers, autoimmune diseases (e.g. Sjogren's syndrome), systemic diseases (e.g. Diabetes, HIV), and anxiety.

Dry mouth has a significant negative impact on a patient's daily life by causing problems such as difficulty chewing, swallowing and speaking, bad breath, dental caries, and periodontitis.

Current dry mouth therapies include two main approaches: a) drugs such as Pilocarpine™ (that can have numerous side effects involving gastrointestinal, cardiovascular, respiratory and urinary systems, and can be administered only for short time periods), and b) artificial saliva (also called saliva substitutes) which can be used to replace moisture and lubricate the mouth. Prior art artificial saliva products require frequent application (every 1-2 hours), are unpleasant, unable to control night-time symptoms, and have low patient compliance.

Commercially available artificial saliva products come in a variety of formulations including solutions, sprays, gels, and lozenges. In general, they contain a polymer agent to increase the thickness, minerals such as calcium and phosphate ions and fluoride, preservatives such as methyl- or propylparaben, and flavoring and related agents. Some of these saliva substitutes have a protein or enzyme-system based formulation. There are also numerous saliva substitutes in the market that have a very low pH (for example, Mouth Kote™ has a pH of 3), and they exhibit a distinct dental erosive potential. Patients are giving negative reviews for existing products.

As such, there remains a need to provide dry mouth treatments and related products, such as artificial saliva gels, that can overcome the shortcomings of the prior art.

SUMMARY

The present disclosure relates to an artificial saliva gel and uses thereof to treat or ameliorate dry mouth (xerostomia). The gel can be of a high viscosity that is maintained at body temperature or when exposed to bodily fluids (for instance, saliva). In some embodiments, the gel can act as a lubricant. Although water-based, the gel can be hydrophobic and not readily dissolvable in bodily fluids. In some embodiments, the gel can be sterile, safe for long-term repeated ingestion, and include a preservative. In some embodiments, the gel can comprise a dental agent for inhibiting growth of dental microorganisms. In order to achieve sterility while maintaining a desired viscosity range, the gel can include a viscosity stabilising agent such as a viscosity protection agent for protection from radiation induced breakdown.

Gel forms of artificial saliva products have consistently been rated better than sprays and mouth rinses in terms of symptom relief, duration of action, convenience, and perceived value. The primary mode of action of artificial saliva products is physical (not pharmacological) by helping to retain moisture to help keep the oral tissues feeling moist, and by creating a physical coating film to lubricate the oral mucosa, thus helping to relieve dry mouth symptoms.

The artificial saliva gel formulations described herein have several unique properties, namely high viscosity, muco-adhesive nature, moisture retaining, near-neutral pH, safety if ingested repeatedly or long-term. In some embodiments, the gel can be sterile or sterilized, and may or may not be tasteless. This artificial saliva gel can have applications such as use in patients that suffer from dry mouth.

Gels, and the uses thereof, as disclosed herein can solve or ameliorate the medical need for a product that provides long-lasting relief from dryness of the mouth. Certain advantages over other gels can become apparent, namely more effective muco-adhesive and lubricant properties leading to better retention of moisture in the oral cavity, longer duration of action, less frequent applications (which can result in higher patient compliance), and lower costs as compared with existing commercial products. In addition, the gel can be tasteless, which can lead to a reduction of saliva protection in response to a taste and therefore reduce the chance of the gel being washed away.

In some embodiments, the gel can have a lower viscosity that would allow the gel to flow and be used as a near-liquid artificial saliva (mouthrinse) or as a spray artificial saliva.

In some embodiments, the gel can comprise a synthetic polymer or a combination of synthetic polymers such as Carbomer Homopolymer Type B (for example, Carbopol 974P NF or Carbopol 5984 EP) or Carbomer Homopolymer Type C (for example, Carbopol 980 NF). As a highly cross-linked polyacrylic acid polymer, these synthetic polymer types have been shown to have good muco-adhesive properties. In addition, a second polymer (such as a natural polymer) for example CNC (nano-crystalline cellulose) can be added to the carbomer, or the CNC can replace the Carbomer Homopolymer Type B or Type C. Accordingly, the thickening/gelling/viscosity agent, can be selected from the group consisting of Carbomer Homopolymer Type B, Carbomer Homopolymer Type C, CNC, or a combination thereof.

The term "CNC", as used herein, can refer to Cellulose Nanocrystals, Crystalline Nanocellulose, which is also known as Nanocrystalline Cellulose (NCC). CNC can be a polymer and can comprise nanoparticles in some embodiments.

CNC can have cross-linkage properties and can disperse in water. Polymeric systems based on cellulose can show unique properties such as biocompatibility, biodegradability, and biological functions.

Use of CNC according to the present disclosure, can provide for at least two new and unexpected behaviours:

a) addition of small amounts of CNC can maintain high viscosity of a carbomer based artificial saliva gel after undergoing gamma radiation sterilization. Adding CNC can reduce or prevent a gel viscosity drop observed during shelf life testing post irradiation. In addition, to achieving a high viscosity pre and post radiation, the use of small concentrations of CNC can allow the use of less highly cross-linked Carbopols™. For example, there are various grades of Carbopols™ available, some with higher cross-linking than others.

b) gels made of only CNC (no carbomer) and water increased gel viscosity after exposure to gamma radiation.

The state of the art does not teach:

a) the use of CNC as an additional gelling agent in carbomer based artificial saliva gels. The use of CNC as an additional component (a few % by mass being added) in artificial saliva gel based on a carbomer gelling agent (such as Carbopol™) can increase the viscosity of the resulting artificial saliva gel;

b) the use of CNC as a protection agent in carbomer based artificial saliva gels against the loss in viscosity caused by gamma radiation sterilization. Where CNC is added to an artificial saliva gel based on a carbomer gelling agent (such as Carbopol™), and the gel is sterilized using gamma radiation, the resulting post radiated gel can remain much more viscous (for example, twice as viscous) as compared with a post radiated gel that did not have any CNC added; and c) the thickening behavior of CNC gels (CNC without carbomer) when irradiated during gamma radiation sterilization. CNC gels (without carbomer) can increase their viscosity when irradiated with gamma rays, and this can provide a method to obtain high viscosity artificial saliva gels post radiation, and control the viscosity post radiation by controlling the radiation dose and the initial CNC concentration in pre-radiation gel.

Regarding the term "Carbopol™", as used herein, can refer to high molecular weight, crosslinked polyacrylic acid polymers. Carbopols™ can differ by crosslink density and can be grouped as homopolymers or copolymers. Carbopol™ homopolyers can be polymers of acrylic acid crosslinked with allyl sucrose or allyl pentaerythritol. Carbopol™ 974P NF is a homopolymer (acrylic acid crosslinked with allyl pentaerythritol). Carbopol™ copolymers can be polymers of acrylic acid and C10-C30 alkyl acrylate crosslinked with allyl pentaerythritol.

The term "carbomer", as used herein, is a generic (i.e. nonproprietary) name adopted by USP-NF, United States Adopted Names Council (USAN) and CTFA for various Carbopol™ polymers. As such Carbopol™ 974P NF and Carbopol™ 5984 EP can be referred to as a carbomer homopolymer Type B. In addition, Carbopol 980 NF can be referred to as a carbopol homopolymer Type C. Carbomers 71G and 971P NF are categorized as Homopolymer Type A, while 974P NF is Type B, and 980 NF is Type C based on their viscosity characteristics.

Broadly stated, in some embodiments, an artificial saliva gel is provided, comprising: water; a thickening agent for thickening the water into a gel; a neutralizer for setting the gel viscosity and adjusting a pH level of the gel; a viscosity agent for reducing changes of gel viscosity due to radiation exposure; and a preservative for preserving the gel; wherein the gel can be safely used internally or orally.

In some embodiments, the viscosity agent can comprise nanoparticles, CNC, and/or glycerin. In some embodiments, the thickening agent comprises a carbomer, a Carbopol™, and/or carbomer homopolymer Type B (Carbopol™ 974P NF) or Type C (Carbopol™ 980 NF). In some embodiments, the neutralizer comprises a base selected from the group consisting of potassium hydroxide, sodium hydroxide, and triethanolamine and the pH level of the gel is between 5.8 and 6.4. In some embodiments, the preservative comprises a food grade preservative and/or potassium sorbate. In some embodiments, the gel further comprises a dental agent for inhibiting growth of dental microorganisms, such as, but not limited to a sugar alcohol, such as, but not limited to, xylitol. In some embodiments, the gel further comprises a colourant for colouring the gel. In some embodiments, the gel can further comprise a flavoring compound for flavoring the gel. In some embodiments, the gel can have a low, near-liquid viscosity.

Broadly stated, in some embodiments, a use of a gel for artificial saliva is provided, the gel comprising: water; a thickening agent for thickening the water into a gel; a neutralizer for setting a viscosity of the gel and adjusting a pH level of the gel; and a preservative for preserving the gel; wherein the viscosity of the gel is similar to saliva and can be safely used orally.

Broadly stated, in some embodiments, a method of treating dry mouth with an artificial saliva is provided, the method comprising: providing the artificial saliva, the artificial saliva comprising: water; a thickening agent for thickening the water into a gel; a neutralizer for setting a viscosity of the gel and adjusting a pH level of the gel; and a preservative for preserving the gel; wherein the viscosity of the gel is similar to saliva and can be safely used orally; applying the artificial saliva to a mouth to be treated; and allowing the artificial saliva to address the symptoms of dry mouth.

In some embodiments, the artificial saliva can provided in the range of one to two mL. In some embodiments, the artificial saliva is applied directly on a tongue of the mouth to be treated. In some embodiments, the artificial saliva is spread thoroughly inside the mouth. In some embodiments, the artificial saliva is reapplied as desired by the subject. In some embodiments, the artificial saliva is reapplied daily. In some embodiments, the artificial saliva is reapplied for four or more times per day. In some embodiments, the subject is a non-human subject. In some embodiments, the artificial saliva is provided from a single-use package. In some embodiments, the single-use package is sterile. In some embodiments, the artificial saliva is provided as a spray. In some embodiments, the artificial saliva is swallowed by the subject. In some embodiments, the artificial saliva is applied once for overnight use, without reapplication.

Broadly stated, in some embodiments, an artificial saliva is provided comprising: water; a thickening agent for thickening the water into a gel; a neutralizer for setting a viscosity of the gel and adjusting a pH level of the gel; and a preservative for preserving the gel; wherein the gel has a high viscosity and strong muco-adhesive properties and can be safely used orally.

Broadly stated, in some embodiments, a kit for treating dry mouth with artificial saliva is provided, the kit comprising, an artificial saliva gel, as described herein, and instructions for use of the gel.

BRIEF DESCRIPTION OF THE DRAWINGS

FIG. 1 is a block diagram depicting an embodiment of an artificial saliva gel.

DETAILED DESCRIPTION OF EMBODIMENTS

The present disclosure relates to an artificial saliva gel and uses thereof to treat or ameliorate dry mouth (xerostomia). The gel can be of a high viscosity that is maintained at body temperature or when exposed to bodily fluids (for instance, saliva). In some embodiments, the gel can act as a lubricant. Although water-based, the gel can be hydrophobic and not readily dissolvable in bodily fluids. In some embodiments, the gel can be sterile, safe for long-term repeated ingestion, and include a preservative. In some embodiments, the gel can comprise a dental agent for inhibiting growth of dental microorganisms. In order to achieve sterility while maintaining a desired viscosity range, the gel can include a viscosity stabilising agent such as a viscosity protection agent for protection from radiation induced breakdown.

Referring now to FIG. 1, a block diagram is shown depicting possible components and potential functional characteristics of an embodiment of an artificial saliva gel. In some embodiments, the artificial saliva gel can comprise a thickening agent, water, a neutralizer, a preservative, a viscosity affecting agent/a radiation breakdown protective agent, and/or a dental agent. In some embodiments, the artificial saliva gel can be biocompatible, have near-neutral pH (hence non-erosive), strong muco-adhesive properties, help in retaining moisture in the oral cavity, be safe for ingestion and application over mucous membranes, be insipid, be hydrophobic, be of high viscosity that can be maintained when heated, be of food grade and/or sterile, reduce and prevent oral bacteria and dental decay, have reduced viscosity breakdown following exposure to gamma irradiation, and/or also be a good lubricant.

In some embodiments, the gel can be biocompatible, orally compatible, mucous membrane compatible, and ingestible by humans or animals. The components of the gel can be based on the U.S. Food and Drug Administration (FDA) Generally Recognized as Safe (GRAS) list and/or Food Additive Status list for acceptable ingredients and additives. In some specific embodiments, the gel components can include Carbopol™ 974P NF, water, potassium sorbate, potassium hydroxide, glycerine, CNC, and/or xylitol, with an acidity at a non-irritating level (for example, between pH 5.5 and 7.5, and in some embodiments, pH 6.0). As all gel components can be safe for ingestion and mucous membrane application, the gel will be safe if a patient ingests the gel accidentally or intentionally. In some embodiments, the gel can be food grade, following good manufacturing practice (GMP) or natural health products (NHP) standards, or sterile. The gel can be sterilized by heat (for example, by autoclaving) or other sterilization methods as known in the art (for example, by e-beam or gamma irradiation). In sterile embodiments, the gel can also be used on open wounds. In some embodiments, the gel can be safe for long term repeated ingestion. For example, users can ingest small quantities (a few mL) daily without adverse effects as per FDA's GRAS database. The gels can be excretable by natural pathways or processes. In some embodiments, the gels also do not adversely affect tooth health, gum tissue, or corrode teeth.

In some embodiments, the gel formulation may require additional components in order to maintain its integrity through sterilization, for example gamma radiation sterilization. These stability compounds can include, for example, glycerine (glycerol) or propylene glycol. Glycerol has very low toxicity when ingested and it is used widely in foods, beverages, and personal care preparations. The oral toxicity of propylene glycol is also very low, and it does not cause sensitization.

Different strategies can be used to achieve a gel of a certain viscosity. Glycerine, for example, can be added to an initial gel formulation in order to protect the gel during gamma radiation sterilization. In addition, a sterilizing radiation dosage can be kept as low as practical (for example, a 25-40 kGy standard dose for sterilization used in the industry). Further, increasing the concentration of the polymer (for example Carbopol™) in the gel can result in the radiated gel being thicker.

The above modifications, however, do still not result in a solution to the problem of creating a gel has a target viscosity in the order of 80,000 cPs-100,000 cPs after sterilization with gamma radiation.

Further increases in the concentration of Carbopol™ in the gel to increase its viscosity cannot create a safe internal and ingestible artificial saliva gel as the higher amount of Carbopol™ will be potentially ingested by a patient during each use, leading to safety concerns.

Adjusted gel viscosities can also push the manufacturing of the gel into a less predictable outcome and the manufacturability of such a product is constrained. For example, there is a limit to reducing the radiation dose exposure to the gel while ensuring a minimum exposure of 25 KGy dose. When irradiating the gel, with the minimum exposure set at 25 KGy a feasible dose range is required (while following the VDmax method for sterilization validation). Hence, the gel still will be exposed to a radiation dose much higher than 25 KGy. As such, the industry practice for sterile products is to develop a formulation that remains stable for the maximum gamma radiation dose of 40 kGy or higher, which will ensure that the normal dose of 25-40 kGy used in the industry will always result in post-irradiation products with the desired parameters.

An example is provided using the following terminology and formulations:

a) "Initial Gel" formulation (per 100 g of gel): 1.3 g Carbopol™, 4.29 g of 18% KOH, 0.5 g xylitol, 0.1 g Potassium Sorbate (optional), and the rest demineralized water, all mixed under vacuum; and b) "Adjusted gel" formulation (per 100 g of gel): 1.8 g Carbopol™, 9.5 g glycerine, 4.29 g KOH, 0.5 g xylitol, 0.1 g Potassium Sorbate (optional), and the rest demineralized water, all mixed under vacuum.

The viscosity of the adjusted gel before irradiation can be approximately 94,500 cPs (formulation of 1.3% Carbopol™ with 5% glycerin), however, viscosity can be >100,000 cPs with an increase in Carbopol™ from 1.3 g to 1.8 g. The viscosity of the adjusted gel after irradiation (range 27.6-32.8 kGy) was 85,000 cPs, being on the lower side of a desired range (80,000-100,000). When viscosity was re-measured after a few months, viscosity had decreased significantly. Using frequent viscosity measurements, viscosity continued to decrease and stabilized at around 65,000 cPs after 11 months of storage at room temperature. While this is still considered a thick gel in industry terms, the viscosity is lower than initially desired for oral applications and it has to be thick so that it stays longer on the oral mucous membrane and retains moisture for a longer period, hence becoming more effective in symptom relief, and requiring less frequent application by the user. It will also limit the amount of gel that is washed away by saliva.

While the adjusted gel can still be used as an artificial saliva, a higher viscosity would make the gel more effective in symptom relief and reduce the frequency of application by the user/patient. In contrast, a lower viscosity makes the artificial saliva gel less of an option or fit for the intended use as a gel. For example, the adjusted gel viscosity of 65000 cPs after radiation compares to existing sterile and non-sterile artificial saliva gels on the market (30,000-45,000 cPs).

In some embodiments, a small amount of glycerol (from a few percent to a few tens of percent) can be used to enhance gel resistance to breaking down under larger doses of gamma radiation. For oral use of a gel, a low glycerol concentration (for example, 5%-10%) can be used without significantly sweetening the gel, while allowing the gel to withstand larger dose of gamma radiation (for example 40 kGy) and maintaining the high viscosity of the gel post-irradiation.

In some embodiments, the gels can have antimicrobial properties. For example, the gels can resist microbial growth after the gel package/bottle is opened, and after possible contamination by the environment or end user. In some embodiments, a preservative can be used to inhibit molds, yeasts, and bacteria in the gel. In some embodiments, the gels can have a long shelf life at room temperature. When under proper conditions, some embodiments of the gel can be shelf-stable and will not physically degrade/decompose at room temperature for a period of approximately at least two years and can also be resistant to microbial spoilage for approximately at least two years.

In some embodiments, the gel can both comprise a preservative and also be sterilized as discussed herein. In these embodiments, the combination of preservative and sterilization can provide for additional safety for usage in internal or oral applications.

In some embodiments, the gels can have a high viscosity as would be understood by one skilled in the art. Viscosity can be difficult to quantify and measure and the measurement can be dependent on the measuring apparatus used and the conditions under what the viscosity is measured. Having said that, one skilled in the art would have a working knowledge of the relative viscosity of a gel with high viscosity. The viscosity and pH can be of an appropriate level to be comfortable and non-irritating to a user. In addition, in some embodiments, the viscosity of the gel is not significantly affected/reduced when the gel warms up in contact with tissue/gums/saliva.

In some embodiments, the gels can be tasteless (insipid) and do not stimulate salivary glands. The absence of taste in the mouth can reduce transient excessive salivary stimulation, hence decreasing the amount of gel being washed away by saliva. Therefore, the gel can stay longer in the oral cavity. In addition, the absence of taste can allow users to better tolerate the gel in their mouths over a longer period of time. In some embodiments, the gel can be mildly unpleasant in the mouth. As such, patients/users would be less likely to intentionally consume the gel. In some cases, slight fragrance or flavors can be added in the gel to provide a better usage experience to the patient/user.

In some embodiments, the gel manufacturing process can be done under vacuum to reduce/eliminate air trapped in the gel. The gel can be produced free of, or with a reduced amount of, air bubbles. In some embodiments, this characteristic can be achieved by vacuum mixing and manipulation during manufacturing.

Undissolved polymer or other insoluble particulate material can be avoided by thorough mixing, general adherence to GMP practices, and by using high grade compounds such as use of National Formulary (NF) standard compounds.

To achieve some or all of these properties, in some embodiments, the gel can comprise water, a neutralizer, a gelling/thickening agent, a preservative, a viscosity affecting agent, a radiation protective agent, a dental agent, and/or a colourant. In some embodiments, the colorant can be, for example, FD&C (Food, Drug, and Cosmetic) Green 3 colour powder, although any other safe colourant known in the art could be used.

In some embodiments, the gel can be water-based, but not water soluble (hydrophobic) and therefore not readily dissolved by saliva. In addition, some embodiments of the gel do not dry out easily. In some embodiments, the water used in the gel can be demineralized, degassed, distilled and/or reverse osmosis. In addition, the water can be free of salts or alkali, as the presence of electrolyte can significantly reduce the viscosity of the gel. The water used in the gel can have low or acceptable levels of minerals, bacteria, etc. as would be known in the art.

In some embodiments, a neutralizer can be used to neutralize the pH of the gel to a biologically acceptable level. In some embodiments, a base can be used as a neutralizer, for instance potassium hydroxide (KOH), sodium hydroxide (NaOH), or triethanolamine. An appropriate amount of base can be used to obtain a final gel pH similar to saliva, in the range of 6.5+/−1, or in the range of 6+/−0.5. In some embodiments, KOH can be used (instead of NaOH) in order to minimize the viscosity loss/reduction due to the neutralizer, thereby maintaining high viscosity of the gel.

In some embodiments, the gel formulation can contain a gelling/thickening agent to increase the viscosity of the gel. In some embodiments, the gelling/thickening agent can be a carbomer. In some cases, the carbomer can be a Carbopol™. As known in the art, there are a variety of Carbopol™ polymer grades which differ in the performance characteristics (U.S. Pat. No. 4,002,221 by Buchalter, incorporated by reference herein in its entirety). In some cases, the Carbopol™ can be a highly cross-linked polymer such as a Carbopol™ 974P NF. Carbopol™ 974P NF can provide low irritancy and non-sensitizing properties. In addition, Carbopol™ 974P NF is generally not bio-absorbed or metabolized in the body due to the high molecular weight and can be cross-linked exhibiting high viscosities. Carbopol™ 974P NF concentrations of 0.1% to 5% by weight in the gel can be used in some embodiments to provide suitable viscosity for oral, or mucous membrane, use. As known in the art, these percentages can be measured as being relative to the weight of the water. That is, adding 1 gram of polymer to 100 grams of water would likely be known to those versed in the art as "1%". It can also be possible however, that one could have an alternate opinion, that a 1% solution is 1 gram dissolved in 99 grams of water, as this would have a total mass of 100 grams, giving what may be interpreted as a 1% solution. In this case, either interpretation can be allowed. In some embodiments, the Carbopol™ 974P NF concentration can be 1.3-1.8% by weight in the gel.

Carbopol 974P differs from other carbomers in the following ways:

a) Solvent used/safety: A significant area of difference among carbomers is the solvent system used to synthesize them.

"Traditional" polymers are synthesized in benzene (carcinogenic), such as 934 NF, 934P NF, 940 NF, 941 NF, 1342 NF. There are regulatory restrictions on the use of benzene in pharmaceutical formulations. In addition, according to Guidance for Industry Q3C guidelines, Benzene is grouped into Class 1 (Human Carcinogens).

"Toxicologically preferred" polymers are synthesized in either ethyl acetate or a cosolvent (ethyl acetate/cyclohexane mixture). As cyclohexane is classified as Class 2 solvents (non-genotoxic animal carcinogens or possible causative agents of irreversible toxicity, such as neurotoxicity or teratogenicity), Carbomers such as 980 NF, 981 NF, 5984 EP, ETD 2020 NF, Ultrez 10 NF were not desirable in the present gel applications.

Three carbomers (namely 71G NF, 971P NF, and 974P NF) use only Ethyl Acetate as a polymerization solvent.

b) Viscosity: Among the three carbomers mentioned above (71G NF, 971P NF, and 974P NF), the viscosity of Carbopol 974P NF is 3-4 times higher than that of Carbopol 71G NF or 971P NF.

c) Mucoadhesion: Carbopol 974P NF has the highest mucoahesive strength.

As such Carbopol™ 974P can be used in the present gels for the these reasons:

1. It is safe for use in an oral cavity where the gel can be potentially ingested over a period of time (for use as artificial saliva, a patient will continue ingesting small amounts of this gel daily over many years). Carbopol™ 974P NF is the safest high viscosity polymer for long-term ingestion as, unlike other polymers, the only residual solvent present is the ethyl acetate. Ethyl acetate is found naturally in some foods and is GRAS as a direct food additive.

2. Among the carbomers that are safe for oral use, carbomer 974P has the highest viscosity for any given amount added to water. Further meaning that to achieve the same level of viscosity, the least amount of carbomer is used when using carbomer 974P, which further contributes to safety.

3. Among the carbomers that are safe for oral use carbomer 974P has the highest mucoahesive strength for any given amount added to water.

Other synthetic polymers could also be uses, such as Carbomer Homopolymer Type C (for example, Carbopol 980 NF) or the other Carbomer Homopolymer Type B (Carbopol 5984 EP). As 980 NF and 5984EP are produced using two solvents, ethyl acetate and cyclohexane, the cyclohexane residual solvent is less desired for long-term ingestion (as compared to ethyl acetate residual solvent). Cyclohexane is relatively non-toxic and is only acceptable for use as an indirect food additive. However, 980NF and 5984 EP can be used safely orally and ingested repeatedly for medium-term or short term. One of the advantages of using 980 NF would be to obtain a higher viscosity gel that would be used for a shorter period of time as compared with 974P NF. 5984 EP would result in a similar viscosity as 974P NF for a given carbomer concentration percentage, but if the duration of repeated ingestion is only medium-term, then it can be used as an alternate synthetic polymer to 974P NF.

In addition, Glycerin can be used to protect the gel from decreasing in viscosity after exposure to gamma irradiation.

In some embodiments, a preservative can also be added to the gel to preserve the gel and increase its safety for mucous membrane application. In some embodiments, the preservative can be a food grade preservative, for example, potassium sorbate, parabens, or monolaurin. Potassium sorbate can be used in the range of 0.01% to 1% of the gel to provide suitable preservation against common pathogens for a pH in the range of 3 to 6.5, or in the range of 6+/−0.5, which is also a common acidity range for saliva. In addition, other preservatives such as parabens can be used if a higher pH range is desired (for example, from pH 3 to 9). In some embodiments, the potassium sorbate concentration can be 0.1%. An acceptable daily ingestion intake of potassium sorbate can be 875 mg daily for an average adult of 70 kg. For some oral applications, only few grams of the gel can be used per day (for example, an estimated 3-5 grams per day). Assuming full ingestion and a potassium sorbate concentration of 0.1% of the gel, the daily dose would be on the order of few milligrams, which is well below the acceptable daily ingestion of 875 mg.

In some embodiments, a dental agent can be used in the gel to provide added dental benefits to a user/patient when the gel is used orally. In some embodiments, the dental agent can be a sugar alcohol. In some embodiments, the sugar alcohol can be xylitol. The dental agent can provide an additional treatment/therapeutic effect to a user/patient by preventing/reducing dental/oral bacteria and/or respiratory infections. For preventing dental decay, sugar alcohol, for instance xylitol in the range of 0.1% to 5% has been shown to reduce oral bacterial flora (for example *Streptococcus mutans*) and can lead to reduced risk of dental cavities and improved oral and dental health. A preferred concentration to reduce and prevent dental decay is 0.5% (this concentration was used in Kontiokari, T. et al. 1995. "Effect of Xylitol on Growth of Nasopharyngeal Bacteria In Vitro", Antimicrobial Agents and Chemotherapy. 39:1820, incorporated by reference herein in its entirety). Xylitol was also shown (same reference) to reduce bacteria in nasopharyngeal flora and reducing respiratory infections (for example inhibiting the growth of *Streptococcus pneumoniae*). In addition, xylitol is known to also have food preservation properties inhibiting the growth of microorganisms such as *Clostridium butyricum, Lactobacillus bulgaricus, Saccharomyces cerevisiae, Escherichia coli, Salmonella typhi* (Makinen, K. K. and Soderling, E. 1981. "Effect of Xylitol on Some Food-Spoilage Microorganisms", Journal of Food Science. 46:950, incorporated by reference herein in its entirety).

In some embodiments, a colorant (food, drug and/or cosmetic grade) could also be added to the gel if a colored gel is desired.

In some embodiments, CNC can be added to an "Adjusted Gel" formulation to increase overall viscosity of the gel, as well as to prevent breakdown of gel during irradiation, leading to a much lower decrease in overall viscosity post-irradiation. In some embodiments, both glycerin and CNC can be added together to an initial formulation for better protection from breakdown due to irradiation.

A CNC gel sample, as shown in Table 1 below, can be formulated by mixing Carbopol™ in water, allowing the mixture to stay overnight, then neutralizing with 18% KOH solution, followed by addition of CNC. In CNC gels samples without Carbopol™, CNC can be simply mixed in water, followed by pH adjustment by adding a small amount of KOH solution. Glycerin can also be added as a final additive. The above gel samples can also have xylitol added as a dental agent, and potassium sorbate as a preservative.

An effect on post-radiation viscosity can also seen in a CNC hydrogel (i.e. no Carbopol in the formulation). CNC can accelerate the formation of hydrogels and can increase the effective crosslink density of hydrogels. CNC can be not only a reinforcing agent for hydrogel, but can also act as a multifunctional cross-linker for gelation. Glycerin would not be required to protect the vicocity of a CNC gel (without Carbopol) crosslinked through the gamma radiation, but the glycerin in this instance will reduce or slow down the gel solubility in water or saliva.

Other concentrations of the gel components can also be used to obtain similar desired properties and results.

With regard to packaging and uses, the gels can be packed in sachet bags (for single or multiple uses), tubes (for single or multiple uses), or in bottles (squeeze bottles or bottle with pump), although any other appropriate packaging and/or dispensing means, as apparent to one skilled in the art, could be used. Prior art gel formulations, that risk spoilage and/or contamination with undesired microbes when the package is opened and exposed to air, are generally available in small, sterile pouches for single use. These are commonly used as lubricants or in situations where sterility is desired. As such, these prior art gel formulations are limited to single-use packaging. By contrast, some embodiments of the present gels do not have the same risk of spoilage, degradation, or contamination and can be packaged for multiple uses, adding increased convenience for the manufacturer and the user. In some embodiments, the intended uses of the presently disclosed gels do not necessarily require sterility.

The gels as described herein can be used as artificial saliva. Further, methods are provided for the treatment of dry mouth in a subject with artificial saliva, for example, the gels described herein. The artificial saliva would be applied to the mouth of the subject and would be allowed to address the symptoms of dry mouth. While the gels and uses thereof described herein are generally applicable to human treatment and therapy, the gels and uses thereof can also be applicable to veterinary applications. In general, a subject would refer to a human subject with symptoms of dry mouth, although non-human subjects can also be treated.

The artificial saliva can be provided in any desired amount. During each use, pursuant to the patient's preference, approximately 1, 2, or 2.5 mL of artificial saliva gel can be applied by the patient directly on their tongue and spread thoroughly inside the mouth. Any excess gel left in the mouth can be spit out by the patient. Some subjects can use the gel multiple times per day. In some cases, subjects can use the gel for greater than four times per day. In some embodiments, a subject can use the gel between four and eight times per day, although it would be understood that the gel could be used as required. In some embodiments, the gel can be used overnight without reapplication. The artificial saliva can be reapplied as desired by the subject. In addition to alleviating the symptoms of dry mouth (in the mouth), the gels can also alleviate the symptoms of dry throat.

In some embodiments, the gel can be packaged in single-use pouches, tubes, or bottles. In low viscosity, near-liquid embodiments, the near-liquid gel can be packaged in single-use pouches, bottles (mouthwash), or sprays. If the gel or liquid is packaged in single-use pouches, the amount can be be sufficient for a single use. In some embodiments, the amount can be about 2 g (or 2 ml), but 1 g (ml) to 5 g (ml) can be used. Single-use pouches can also be sterilized using gamma radiation. In this case, if the gel is sterile and provided sealed (the pouches are sealed) then no preservatives are required to add to the formulation. If the product (liquid or gel) is provided in single-use pouches, then the patient can squeeze the content of the pouch on their tongue, and then spread it inside the mouth with their tongue.

If the gel is provided in multiple use packaging (tube, spray), then a preservative can be used in most cases (unless the product is to be used up over a short period of time following the unsealing of the package).

If the product is provided liquid in a bottle, then the subject can pour 1-5 ml in a small cup and then rinse their mouth with the liquid. They can spit out the excess after they have rinsed their mouth.

If the product is provided liquid in a spray, the patient can spray the product inside the mouth until a sufficient amount is provided to coat the mouth to their preference.

For the case of using the gel for try/sore throat, the patient can swallow the product (liquid or gel) in order to coat the throat. The subject can minimize or avoid drinking liquids after the gel is used to coat their mouth or throat. If the product (saliva or gel) is washed away, to the subject can reapply it.

In addition, the gels can be used in general to improve denture comfort and as a vehicle for chemical/pharmaceutical agents aimed at improving tooth and gum sensitivity.

Furthermore, the artificial saliva gels can be used for preventing or reducing oral cavities in patients wearing clear aligners for orthodontic treatment. Applying a thin layer of the gel inside the clear aligner tray before every time the tray is placed in the mouth will reduce or prevent dental cavities that could form under the trays due to reduced natural saliva flow inside the tray.

Without any limitation to the foregoing, the present gels, uses, and methods are further described by way of the following examples.

Example 1

Materials
Materials: Purified Water 1100 g, Carbopol 974P NF 13 g, Potassium Hydroxide 18 g, Club House™ green food colour 1 mL, Xylitol 5 g, Potassium sorbate 1 g, glycerine 50 g.

Equipment: Clock/Timer—calibrated, Vacuum pump, 5/16" ID vacuum tubing, Vacuum chamber, Top-loading balance (0.1 g precision), pH meter+electrode, Brookfield™ viscometer.

General Supplies: Calculator, Spatula, Scoopula, Mixing vessel (e.g. large jar or vat), Weighing paper, 50 mL plastic syringe—Luer-lock, Dropper bottle with dropper, Kim Wipes™, Paper towels, Label sheets, Pen, Felt marker, Anti-static brush, 50 mL beaker, Broad spatula.

Example 2

Production
Note that in some embodiments, mixing steps can be performed under vacuum so as to minimize gas/bubbles in the gel. If water or solutions are not previously degassed, the water or solution can be degassed prior to use so as to minimize gas/bubbles in the gel.

Prepare 18% KOH(aq) neutralizer: Weigh out 100 grams pure water into a small beaker. Weigh out 18 grams solid KOH into a beaker or onto a weighing paper. Slowly add solid KOH to water, allow to dissolve with occasional stirring (glass rod or plastic spatula). When fully dissolved, pour mixture into dropper bottle labelled as "18% KOH(aq)".

Prepare gel dispersion: Weigh out 900 grams water into mixing vessel (eg. 1000 mL beaker). Weigh out 5 grams xylitol. Dissolve xylitol in water with stirring. Weigh out 1 gram potassium sorbate. Dissolve potassium sorbate in xylitol solution above. Weigh out 13 grams Carbopol™ 974P NF. CAUTION: This material is a fluffy, lightweight powder. Ensure that any air currents are minimized and that all weighing surfaces are static free. Static can be minimized by light brushing of contacting surfaces with anti-static brush. Add Carbopol™ powder to potassium sorbate/xylitol solution above, with gentle manual mixing using a spatula. Allow the gel to hydrate, for example by allowing it to sit covered overnight in order to hydrate. *NOTE: the gel hydration can also be sped up by adding the Carbopol™ powder to a spinning volume of water, as with a magnetic stirrer.

Prepare gel: Add 42.9 grams of KOH solution above to a small beaker or other transfer vessel. The neutralizer solution should be added in a weight ratio of 3.3 grams neutralizer per gram of Carbopol™ powder. Add 42.9 grams KOH neutralizer solution to gel dispersion with manual stirring using broad spatula. Finally, add 50 g of glycerine to the gel dispersion. Mix until homogeneous gel is achieved. *NOTE: the gel will be highly viscous, making convection very difficult. Because of this, the mixing requires a lot of physical mixing. Unless the entire volume of the gel is thoroughly mixed, there will be regions of differing pH. Confirm pH is approximately 6.0 using a standard pH meter. With a pH meter, after calibrating the meter, dip the electrode into the gel and stir it around briefly to coat the electrode in gel, then take a reading. Take a few readings, mixing in between. If the readings are inconsistent, mix the gel thoroughly and check again. If the readings were inconsistent on a sample volume, then it is likely that the entire batch is not properly mixed. Target pH=6.0±0.2. If the pH is low, add neutralizer in appropriate increments until pH is in correct range. Note that the readings will not be consistent without extremely thorough mixing. If desired, add an acceptable colourant to the gel, for example add FD&C (Food, Drug, and Cosmetic) Green 3 colour powder to gel. Mix until colour is evenly dispersed. Some embodiments may involve addition of a flavoring agent to the gel. This will take thorough mixing with a broad spatula, or mixing by pallets in an industrial mixing chamber, under a vacuum.

Degas gel: The degassing step is intended to remove bubbles introduced in the formulation process. Place the gel in an open container. Place this container into the vacuum chamber, seal the chamber, and pump down to 600 mm Hg for 10 minutes (stopwatch). Allow the gel to warm up to room temperature before making any further measurements.

A CNC gel sample, as shown in Table 1 below, can be formulated by mixing Carbopol in water, allowing the mixture to stay overnight, then neutralizing with 18% KOH solution, followed by addition of CNC. Glycerin can also be added as a final additive. In CNC gels samples without Carbopol™, CNC can be simply mixed in water, followed by pH adjustment by adding a small amount of KOH solution. Glycerin can also be added as a final additive. The above gel samples can also have xylitol added as a dental agent, and potassium sorbate as a preservative. The gel samples may also have a flavoring and/or a coloring agent.

Packaging and Quality Control: Dispense gel into final packaging, which can be a multiple use packaging like bottles, jars, etc, or single use sterile or non-sterile pouches.

Viscosity testing: The viscosity determined for the gel at pH 6 was 50,000 to 100,000+ mPa·s (or cPs), and 85,000 mPa·s (or cP) in one sample [at 37° C. using Brookfield™ Viscometer LVF, S/N: C3390 spindle #4, 6 rpm]. This can be a target spec, although deviations may occur in different circumstances and when scaling up production. Viscosity can be difficult to quantify and measure and the measurement can be dependent on the measuring apparatus used and the conditions under what the viscosity is measured. Having said that, one skilled in the art would have a working knowledge of the relative viscosity of a gel with high viscosity.

Example 3

Results: Viscosity Testing and Stability

TABLE 1

Effects of Radiation on Viscosity

| Sample* | Gamma radiation dose (kGy) | Pre-radiation viscosity (cPs) | Post-radiation viscosity (cPs) | Formulation used (per 100 g of gel) |
|---|---|---|---|---|
| Initial gel | 40-48 KGy (Maximum Gamma Radiation Level test) | >100,000 | fluid <10,000 | 1.3 g Carbopol, NO glycerine, NO CNC |
| Adjusted Gel | 36.6-41.7 KGy | 94500 | 57,750 | 1.3 g Carbopol, 5 g glycerine, NO CNC |
| Adjusted gel | 27.6-32.8 KGy | 94500 | 85,000 65,000 (after 11 months aging) | 1.8 g Carbopol, 9.5 g glycerine, NO CNC |
| CNC gel 6 | 40-49.5 | >100,000 | 41,000 | 1.3 g Carbopol, 5 g glycerine, NO CNC |
| CNC gel 1 | 40-49.5 | >100,000 | 86,000 | 1.3 g Carbopol, 5 g glycerine, 2 g CNC |
| CNC gel 8 | 40-49.5 | >100,000 | 8000 | 1.3 g Carbopol, NO glycerine, 2 g CNC |
| CNC gel 2 | 40-49.5 | >100,000 | >100,000 | 1.3 g Carbopol, 5 g glycerine, 4 g CNC |
| CNC gel 9 | 40-49.5 | >100,000 | 52,000 | 1.3 g Carbopol, NO glycerine, 4 g CNC |
| CNC gel 3 | 40-49.5 | >100,000 | >100,000 | 1.3 g Carbopol, 5 g glycerine, 6 g CNC |
| CNC gel 10 | 40-49.5 | >100,000 | 91,000 | 1.3 g Carbopol, NO glycerine, 6 g CNC |
| CNC gel 7 | 40-49.5 | appears similar but lower than CNC gel11 | 73,000 | NO Carbopol, 5 g glycerin, 15 g CNC |
| CNC gel 11 | 40-49.5 | 39,000 | >100,000 | NO Carbopol, NO glycerine, 15 g CNC |

*All gel samples from Table 1 were adjusted to have a pH of 6, for example by using 18% Potassium Hydroxide solution. The above samples are water-based, and also contain 0.5% xylitol as a dental agent, and 0.1% potassium sorbate as a preservative.

Example 4

Observations: CNC and Gel Viscosity

Certain observations were made regarding the creation, irradiation, and viscosity testing of the gel samples, as outlined in Table 1.

1) Glycerin can help maintain crosslinking of Carbopol™ gels, but not of pure CNC gels during gamma radiation;

2) CNC can provide crosslinking protection against breakdown due to gamma radiation in the case of Carbopol™ gels with or without glycerin;

3) CNC and glycerin both added to the "Adjusted Gel" formulation can result in gels with the least drop in viscosity after irradiation;

4) Certain concentrations of CNC gels can show an increase in viscosity after irradiation (for example, see results of CNC Sample 11 in Table 1); and 5) Adding glycerin adds a sweet taste to the gel, while adding CNC adds no taste.

Example 5

Conclusions: Crystalline Nanocellulose (CNC) and Gel Viscosity

In some embodiments, CNC can be added to an "Adjusted Gel" formulation to increase overall viscosity of the gel, as well as to prevent breakdown of gel during irradiation, leading to a much lower decrease in overall viscosity post-irradiation. In some embodiments, both glycerin and CNC can be added together to an initial carbomer based formulation for better protection from breakdown due to irradiation.

An effect on post-radiation viscosity can also be seen in a CNC hydrogel (i.e. no Carbopol in the formulation). CNC can accelerate the formation of hydrogels and can increase the effective crosslink density of hydrogels. CNC can be not only a reinforcing agent for hydrogel but can also act as a multifunctional cross-linker for gelation.

The scope of the claims should not be limited by the embodiments as set forth in the examples herein, but should be given the broadest interpretation consistent with the description as a whole.

Although a few embodiments have been shown and described, it will be appreciated by those skilled in the art that various changes and modifications can be made to the embodiments described herein. The terms and expressions used in the above description have been used herein as terms of description and not of limitation, and there is no intention in the use of such terms and expressions of excluding equivalents of the features shown and described or portions thereof, it being recognized that the invention is defined and limited only by the claims that follow.

The teachings provided herein can be applied to other uses, methods, or gels, not necessarily the method described herein. The elements and acts of the various embodiments described above can be combined to provide further embodiments.

These and other changes can be made to the invention in light of the above description. While the above description details certain embodiments of the invention and describes certain embodiments, no matter how detailed the above appears in text, the invention can be practiced in many ways. Details of the method may vary considerably in their implementation details, while still being encompassed by the invention disclosed herein.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification. Accordingly, the actual scope of the invention encompasses not only the disclosed embodiments, but also all equivalent ways of practicing or implementing the invention.

The above description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. The elements and acts of the various embodiments described above can be combined to provide further embodiments.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

We claim:

1. A method of ameliorating the symptoms of a subject with dry mouth or dry throat with an artificial saliva gel, the method comprising:
    providing the artificial saliva gel, the gel comprising:
        water;
        cellulose nanocrystals (CNC), wherein the cellulose nanocrystals are at a concentration of up to 15% of the gel by weight;
        a neutralizer for adjusting a pH level of the gel;
        wherein the gel is free of carbomer;
        wherein the gel has been exposed to gamma radiation;
        wherein the gel has a post-radiation viscosity between 50,000 and 100,000 cPs when measured using a viscometer at 37° C. and at pH 6; and wherein the gel can be safely used orally;
    applying the artificial saliva gel to a mouth to be treated; and
    allowing the artificial saliva gel to address the symptoms of dry mouth or dry throat.

2. The method of claim 1 wherein the artificial saliva gel is provided in the range of one to two mL.

3. The method of claim 1 wherein the artificial saliva gel is applied directly on a tongue of the mouth to be treated.

4. The method of claim 1 wherein the artificial saliva gel is spread thoroughly inside the mouth.

5. The method of claim 1 wherein the artificial saliva gel is provided as a spray.

6. The method of claim 1, wherein the artificial saliva gel further comprises a preservative.

7. The method of claim 1, wherein the gel is applied between one and eight times per day.

8. The method of claim 1, wherein the gel is applied once for overnight use, without reapplication.

9. An artificial saliva gel comprising:
    water;
    cellulose nanocrystals (CNC), wherein the cellulose nanocrystals are at a concentration of up to 15% of the gel by weight;
    a neutralizer for adjusting a pH level of the gel;
    wherein the gel is free of carbomer;
    wherein the gel has been exposed to gamma radiation;
    wherein the gel has a post-radiation viscosity between 50,000 and 100,000 cPs when measured using a viscometer at 37° C. and at pH 6; and wherein the gel has strong muco-adhesive properties and can be safely used orally.

10. The artificial saliva gel of claim 9, further comprising glycerin.

11. The artificial saliva gel of claim 9, wherein the neutralizer comprises a base selected from the group consisting of potassium hydroxide, sodium hydroxide, and triethanolamine.

12. The artificial saliva gel of claim 9, further comprising a preservative.

13. The artificial saliva gel of claim 9, further comprising a dental agent for inhibiting the growth of dental microorganisms, the dental agent comprising xylitol.

14. The artificial saliva gel of claim 10, wherein the glycerin is at a concentration of at least 5% of the gel by weight.

15. A kit for treating dry mouth with artificial saliva is provided, the kit comprising, the artificial saliva gel of claim 9 and instructions for use of the artificial saliva gel.

16. An artificial saliva gel comprising:
water;
cellulose nanocrystals (CNC), wherein the cellulose nanocrystals are at a concentration of between 2% and 15% of the gel by weight;
carbomer, wherein the carbomer is at a concentration of between 0.1% and 5% of the gel by weight;
glycerin, wherein the glycerin is at a concentration of between 5% and 10% of the gel by weight;
a neutralizer for adjusting a pH level of the gel;
wherein the gel has been exposed to gamma radiation;
wherein the gel has a post-radiation viscosity between 50,000 and 100,000 cPs when measured using a viscometer at 37° C. and at pH 6; and wherein the gel has strong muco-adhesive properties and can be safely used orally.

17. The artificial saliva of claim 16, wherein the cellulose nanocrystals are at a concentration of between 2% and 6% of the gel by weight.

18. The artificial saliva of claim 16, wherein the carbomer is at a concentration of 1.3% of the gel by weight.

19. The artificial saliva of claim 16, wherein the glycerin is at a concentration of 5% of the gel by weight.

* * * * *